United States Patent [19]

Papenfuhs et al.

[11] Patent Number: 5,973,189
[45] Date of Patent: Oct. 26, 1999

[54] MONOESTERS OF CARBOXYMETHYLENE ANTHRANILIC ACIDS AND PROCESS FOR PREPARING THE SAME

[75] Inventors: Theodor Papenfuhs, Frankfurt; Ralf Pfirmann, Griesheim; Doris Neumann-Grimm; Stefan Krause, both of Frankfurt, all of Germany

[73] Assignee: Clariant GmbH, Frankfurt, Germany

[21] Appl. No.: 09/029,594

[22] PCT Filed: Aug. 19, 1996

[86] PCT No.: PCT/EP96/03631

§ 371 Date: Jul. 16, 1998

§ 102(e) Date: Jul. 16, 1998

[87] PCT Pub. No.: WO97/08131

PCT Pub. Date: Mar. 6, 1997

[30] Foreign Application Priority Data

Aug. 31, 1995 [DE] Germany .......................... 195 32 053
May 14, 1996 [DE] Germany .......................... 196 19 395

[51] Int. Cl.⁶ .................................................. C07C 229/56
[52] U.S. Cl. ................................................................ 560/43
[58] Field of Search ................................................ 560/43

[56] References Cited

U.S. PATENT DOCUMENTS

| | | | |
|---|---|---|---|
| 4,734,419 | 3/1988 | Hashimoto et al. | 514/259 |
| 4,883,800 | 11/1989 | Hashimoto et al. | 514/259 |
| 5,093,364 | 3/1992 | Richards et al. | 514/533 |

FOREIGN PATENT DOCUMENTS

| | | |
|---|---|---|
| 0218999 | 4/1987 | European Pat. Off. . |
| 0360417 | 3/1990 | European Pat. Off. . |
| 19532052 | 3/1997 | Germany . |
| 19532053 | 3/1997 | Germany . |

OTHER PUBLICATIONS

Thurs, J. Med. Chem. 1991, 34, 1283.
J. Heterocycl. Chem. 1987, 24, 811.
J. Prakt. Chem. 1929, 120, 64.
J. Heterocycl. Chem. 1977; vol. 14 (7) pp. 1139–43.
Chemical Abstracts vol. 108, 1988 p. 538 108:2213794.
International Search Report reference sheet.
Organic Chemistry 4th ed., Pine, Hendrickson, Cram and Hammond, McGraw–Hill 1980, p. 314, 1980.

*Primary Examiner*—Gary Geist
*Assistant Examiner*—Brian J. Davis
*Attorney, Agent, or Firm*—Scott E. Hanf

[57] ABSTRACT

Compounds have the formula (I),

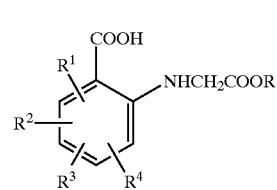

in which R stands for straight-chain or branched ($C_1$–$C_{20}$) alkyl, phenyl or $CH_2$ phenyl, the alkyl group or phenyl group being optionally substituted by halogen, ($C_1$–$C_4$) alkyl, ($C_1$–$C_4$) alkoxy, and $R^1$, $R^2$, $R^3$, $R^4$ independently represent hydrogen, halogen, OH, $NO_2$, ($C_1$–$C_6$) alkoxy, ($C_1$–$C_6$) alkyl or halogen-substituted ($C_1$–$C_6$)-alkyl. Also disclosed is a process for preparing these compounds.

4 Claims, No Drawings

MONOESTERS OF CARBOXYMETHYLENE ANTHRANILIC ACIDS AND PROCESS FOR PREPARING THE SAME

The invention relates to monoesters of carboxymethylene-anthranilic acids and a process for their preparation.

Such monoesters of carboxymethylene-anthranilic acid are not yet described in the literature. Such compounds are valuable starting substances for novel synthesis variants for the preparation of aldose reductase inhibitors—as can be seen from the German patent application (file reference: 195 32 052.2) filed on the same day as the present German patent application (file reference 195 32 053.0)—and render novel classes of compounds, such as, for example, diesters of carboxymethyleneanthranilic acids with various ester radicals, accessible for the first time.

The quite simple and short synthesis route, which starts from 2,4-dichlorobenzoic acid and leads to the quinazolinediones of the formula (A) used as starting substances for the preparation of aldose reductase inhibitors, is represented in simplified form in the following equation:

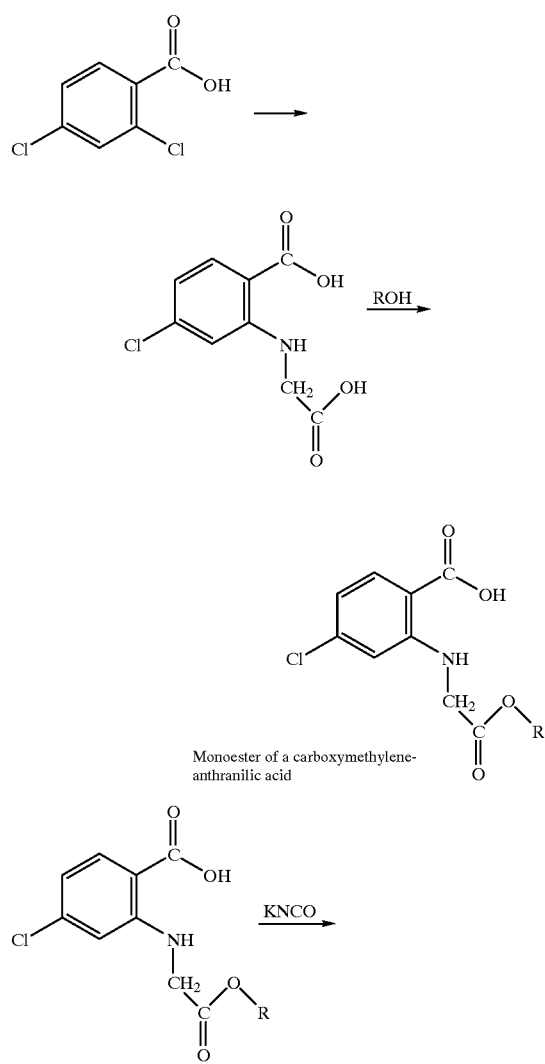

Monoester of a carboxymethylene-anthranilic acid

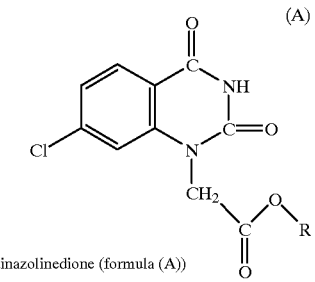

Quinazolinedione (formula (A))

The abovementioned quinazolinedione (formula (A)) is an ester of 1,2,3,4-tetrahydro-2,4-dioxoquinazolin-1-ylacetic acid, which, according to EP 218 999, can be used as a starting material for the preparation of aldose reductase inhibitors.

To extend the possibilities of the synthesis of aldose reductase inhibitors and to render novel compounds accessible, there was therefore a need to provide such compounds.

This object was achieved by compounds of the formula (I)

(I)

[Structure: benzene ring with COOH, NHCH$_2$COOR, and substituents R$^1$, R$^2$, R$^3$, R$^4$]

in which R is straight-chain or branched $(C_1-C_{20})$-alkyl, phenyl or $CH_2$-phenyl, where the alkyl group or phenyl group can also be substituted by halogen, $(C_1-C_4)$-alkyl or $(C_1-C_4)$-alkoxy, and $R^1$, $R^2$, $R^3$ and $R^4$ independently of one another are hydrogen, halogen, OH, $NO_2$, $(C_1-C_6)$alkoxy, $(C_1-C_6)$alkyl or halogen-substituted $(C_1-C_6)$alkyl.

Important compounds of the formula (I) among these are those in which R is straight-chain or branched $(C_1-C_{12})$-alkyl, phenyl or $CH_2$-phenyl, in particular $(C_1-C_6)$-alkyl, preferably methyl or ethyl, and $R^1$, $R^2$, $R^3$ and $R^4$ are hydrogen, fluorine, chlorine, $(C_1-C_4)$alkoxy, $(C_1-C_4)$alkyl or chlorine- or fluorine-substituted $(C_1-C_4)$alkyl, in particular hydrogen, fluorine, chlorine, methyl or ethyl.

The compounds in which two, and in particular three, of the radicals $R^1$, $R^2$, $R^3$ and $R^4$ are hydrogen are of great importance here.

Compounds which are also of importance are those of the formula (II)

(II)

[Structure: benzene ring with COOH, NHCH$_2$COOR, and Cl substituent]

in which R is a straight-chain or branched $(C_1-C_{20})$-alkyl, phenyl or $CH_2$-phenyl, where the alkyl group or phenyl group can be substituted by halogen, $(C_1-C_4)$-alkyl or $(C_1-C_4)$-alkoxy, and in particular the alkyl group can be substituted by halogen or ($C_1$–$C_4$)-alkoxy and in particular the phenyl group can be substituted by ($C_1$–$C_4$)-alkyl or ($C_1$–$C_4$)-alkoxy.

In the compounds of the formula (II), R is, in particular, a straight-chain or branched ($C_1$–$C_{12}$)-alkyl, phenyl or $CH_2$-phenyl, preferably a straight-chain or branched ($C_1$–$C_6$)-alkyl or phenyl. For completeness, it should be mentioned here that the compounds of the formula (II) are monoesters of N-carboxymethylene-4-chloroanthranilic acid.

N-Carboethoxymethylene-4-chloroanthranilic acid and N-carbomethoxymethylene-4-chloroanthranilic acid, N-carboisopropoxymethylene-4-chloroanthranilic acid, N-carbopropoxymethylene-4-chloroanthranilic acid, N-carbobutoxy-methylene-4-chloroanthranilic acid, N-carbohexoxymethylene4-chloroanthranilic acid and N-carbobenzoxymethylene-4-chloroanthranilic acid are of particular interest.

The invention furthermore relates to a process for the preparation of the compounds of the formula (I), which comprises reacting an N-carboxymethylene-anthranilic acid with alcohols ROH in the presence of a catalyst and, if appropriate, of a solvent.

The N-carboxymethyleneanthranilic acid employed in the preparation of the compounds of the formula (I) is described by the formula (III)

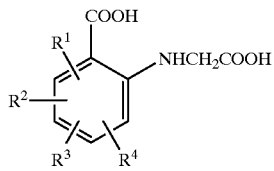

(III)

in which $R^1$, $R^2$, $R^3$ and $R^4$ have the meaning given in formula (I). The radical R in the alcohol ROH has the meaning already given in formula (I).

The reaction can be carried out in the presence or absence of a solvent. Solvents which can be used are aliphatic or aromatic hydrocarbons, for example cyclohexane, toluene or benzene, the alcohol ROH or mixtures thereof. The alcohol ROH is employed in an excess of 1 to 1000 mol, advantageously 1.5 to 500 mol, preferably 2 to 200 mol, per mole of the particular N-carboxymethylene-anthranilic acid.

Dehydrating agents, such as carbonyldiimides, strong inorganic or organic acids or salts thereof or Lewis acids are suitable as the catalyst. Catalysts which have often proved suitable are, for example, dicyclohexylcarbodiimide, N,N-carbonyl-diimidazole, p-toluenesulfonic acid, pyridinium p-toluenesulfonate, trifluoroacetic acid, boron trifluoride, sodium sulfate, sulfuric acid or hydrochloric acid, in particular sulfuric acid or hydrochloric acid, preferably sulfuric acid. Mixtures of the reagents mentioned can be employed analogously. The concentration of the catalyst can be between 0.5 and 100 mol %, advantageously between 1 and 50 mol %, preferably 2 to 30 mol %, based on the particular N-carboxymethylene-anthranilic acid.

The process is particularly simple if 2.5 to 15 mol % of catalyst, based on the particular N-carboxymethylene-anthranilic acid employed, is employed.

According to a preferred variant, 5 to 15 mol % of sulfuric acid in the form of concentrated sulfuric acid is employed, as the catalyst, per mole of carboxymethyleneanthranilic acid.

The reaction is usually carried out at 20 to 200, in particular 40 to 160, preferably 50 to 120° C. These temperatures may necessitate working under pressure. This is the case if the reaction temperature is above the boiling point of the particular reaction mixture.

The reaction temperatures are between 20° C. and the boiling point of the particular alcohol, advantageously between 40° C. and the particular boiling point, preferably between 60° C. and the particular boiling point. Normal pressure can be used for this procedure.

The reaction times are 0.5 to 60 hours, advantageously 0.75 to 30 hours, preferably 1 to 20 hours.

According to a particular process variant, the solvent can also serve as an entraining agent for removal of the water formed during the esterification, for example by azeotropic distillation. Aliphatic and aromatic hydrocarbons, for example n-hexane, cyclohexane, toluene or xylene, aliphatic or cycloaliphatic ketones, for example n-butanone, 4-methyl-2-pentanone or cyclohexanone, and also mono- or polychlorinated aliphatic or aromatic hydrocarbons, for example methylene chloride, chloroform or chlorobenzene, can be used for this purpose. Chloroform is particularly suitable.

Another possibility of removing the water formed during the esterification comprises adding a water-binding agent, for example an ortho-ester, in particular trimethyl orthoformate or triethyl orthoformate. It may be particularly favorable to allow the esterification to proceed up to a certain conversion, for example 50 to 90% or even more, in particular 55 to 75%, and then to add an ortho-ester to bring the reaction to completion.

According to another process variant, the azeotropic distillation can be combined with the addition of a water-binding agent, for example an ortho-ester. In this case also, it may be advantageous to allow the esterification to proceed up to a certain conversion, for example 50 to 90% or even more, in particular 50 to 75%, by means of azeotropic distillation and then to add the water-binding agent, for example an ortho-ester, in order to bring the reaction to completion.

It is particularly surprising that only reaction to give the monoester occurs under these reaction conditions, since only reactions to give the diester are described in the literature.

Thus, J. Med. Chem. 1991, 34, 1283, and J. Heterocycl. Chem. 1987, 24, 811 describe the reaction of carboxymethylene-4-chloroanthranilic acid with methanol and sulfuric acid, and J. Prakt. Chem. 1929, 120, 64 describes the reaction with methanol and hydrochloric acid, to give the diester. In view of this, it is surprising that a monoester is formed with the use of comparatively small amounts of catalyst, and it was furthermore not to be expected that only one of the two possible monoesters forms with a high selectivity.

The process steps described can be carried out under reduced, increased or normal pressure.

The following examples illustrate the invention without limiting it.

EXAMPLE 1

74.5 g (324.8 mmol) of N-carboxymethylene-4-chloroanthranilic acid are suspended in 1660 g of ethanol, 2.9 g (2.96 mmol) of concentrated sulfuric acid are added and the mixture is heated at the boiling point for 10 hours. After a reaction time of 5 hours, the same amount of sulfuric acid is again added. After 10 hours, the ethanol is distilled off and the product which precipitates out is filtered off in the cold and washed with cold ethanol. 55.5 g (0.22 mol, 73%) of N-carboethoxymethylene-4-chloro-anthranilic acid are obtained.

Melting point: 166 to 167° C.; $^1$H-NMR (DMSO-d$^6$): 1.22 (t,CH$_3$ ethyl ester), 4.11–4.21 (m, 2 CH$_2$), 6.64 (dd, H-C(5)), 6.66–6.69 (m, H-C(3)), 7.80 (d, H-C(6)), 8.21–8.36 (NH); MS: 259, 257, 186, 184, 169, 168, 167, 166

The corresponding diethyl ester has formed only in an amount of <0.2%, as detected by HPLC analysis.

EXAMPLE 2

5 g (21.8 mmol) of N-carboxymethylene-4-chloro-anthranilic acid are introduced into 50 ml of methanol, and 222 mg (2.3 mmol) of sulfuric acid are added. The mixture is heated under reflux for 4 hours and then cooled to room temperature. The product which has precipitated out is filtered off with suction, washed with methanol and dried. 4.0 g (16.4 mmol; 75%) of N-carbomethoxymethylene-4-chloro-anthranilic acid are obtained.

Melting point: 201 to 203° C.; MS: 245, 243, 186, 184, 168, 166

EXAMPLE 3

5 g (21.8 mmol) of N-carboxymethylene-4-chloro-anthranilic acid are suspended in 50 ml of isopropanol, and 222 mg (2.3 mmol) of sulfuric acid are added. The mixture is heated under reflux for 8.25 hours. It is then cooled to room temperature and the product which has precipitated out is washed with petroleum ether and dried. 4.6 g (16.9 mmol; 78%) of N-carboisopropoxymethylene-4-chloro-anthranilic acid are obtained.

Melting point: 181° C.; MS: 273, 271, 230, 228, 186, 184, 168, 166

EXAMPLE 4

Preparation of N-carbopropoxymethylene-4-chloro-anthranilic acid

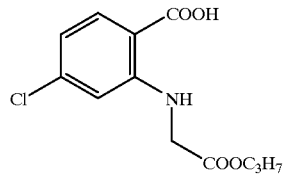

5 g (21.8 mmol) of N-carboxymethylene-4-chloro-anthranilic acid are dissolved in 40 ml of n-propanol, 108 mg (1.05 mmol) of concentrated H$_2$SO$_4$ are added and the mixture is heated at 70° C. for 4.5 hours. It is then cooled to room temperature and the product which has precipitated out is filtered off with suction and washed with n-propanol. After drying, 3.6 g (13.3 mmol; 61%) of N-carbopropoxymethylene-4-chloro-anthranilic acid are obtained as a pale yellow solid.

Melting point: 155° C.

For recording the mass spectrum, the carboxyl group which is still free is esterified with diazomethane, since N-carbopropoxymethylene-4-chloro-anthranilic acid decomposes on the GC column.

MS (methyl N-carbopropoxymethylene-4-chloro-anthranilate): 287, 285, 242, 200, 198, 168, 166.

EXAMPLE 5

Preparation of N-carbobutoxymethylene-4-chloro-anthranilic acid

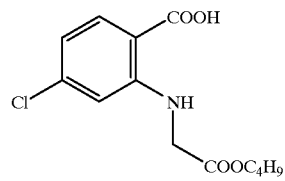

5 g (21.8 mmol) of N-carboxymethylene-4-chloro-anthranilic acid are dissolved in 40 ml of n-butanol. 108 mg (1.05 mmol) of concentrated H$_2$SO$_4$ are added and the mixture is heated at 75° C. for 2 hours. After cooling to room temperature, the product which has precipitated out is filtered off with suction, washed with n-butanol and dried. 4.7 g (16.5 mmol; 76%) of pale yellow crystalline N-carbobutoxymethylene-4-chloro-anthranilic acid are obtained.

Melting point: 130° C.

To record the mass spectrum, the carboxyl group which is still free is esterified with diazomethane, since N-carbobutoxymethylene-4-chloro-anthranilic acid decomposes on the GC column.

MS (methyl N-carbobutoxymethylene-4-chloro-anthranilate): 301, 299, 242, 200, 198, 168, 166.

EXAMPLE 6

Preparation of N-carbohexoxymethylene-4-chloro-anthranilic acid

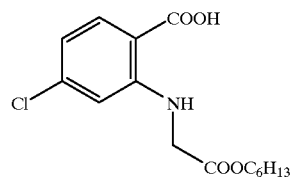

5 g (21.8 mmol) of N-carboxymethylene-4-chloro-anthranilic acid are dissolved in 40 ml of n-hexanol, 108 mg (1.05 mmol) of concentrated H$_2$SO$_4$ are added and the mixture is heated at 75° C. for 2 hours. The reaction mixture is cooled to room temperature and the product is filtered off with suction. Washing with hexanol and drying gives 5.8 g (19.8 mmol; 91%) of carbohexoxymethylene-4-chloro-anthranilic acid as a pale yellow solid.

Melting point: 99° C.

To record the mass spectrum, the carboxyl group which is still free is esterified with diazomethane, since N-carbohexoxymethylene-4-chloro-anthranilic acid decomposes on the GC column.

MS (methyl N-carbohexoxymethylene-4-chloro-anthranilate): 329, 327, 244, 242, 200, 198, 168, 166.

EXAMPLE 7

Preparation of N-carbobenzoxymethylene-4-chloro-anthranilic acid

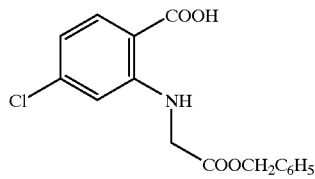

10 g (43.6 mmol) of N-carboxymethylene-4-chloro-anthranilic acid are dissolved in 40 ml of benzyl alcohol, 444 mg (4.3 mmol) of $H_2SO_4$ are added and the mixture is stirred at 110° C. for 2 hours. It is cooled to room temperature and the product which has precipitated out is filtered off with suction, washed with benzyl alcohol and dried. 7.3 g (22.9 mmol; 53% of pale yellow crystalline N-carbobenzoxymethylene-4-chloro-anthranilic acid are obtained.

Melting point: 128° C.

To record the mass spectrum, the carboxyl group which is still free is esterified with diazomethane, since N-carbobenzoxymethylene-4-chloro-anthranilic acid decomposes on the GC column.

MS (methyl N-carbobenzoxymethylene-4-chloro-anthranilate): 335, 333, 244, 242, 200, 198, 168, 166.

EXAMPLE 8

Preparation of N-carboethoxymethylene-4-chloroanthranilic acid with azeotropic distillation of water.

230 g (1.0 mol) of N-carboxymethylene-4-chloro-anthranilic acid are suspended in 218 g of ethanol and 620 g of chloroform, and 11 g (107 mmol) of concentrated sulfuric acid are added. In addition, the amount of chloroform needed to fill a water separator connected to the reaction vessel is added. The mixture is heated under reflux for 7 hours, the water formed during the esterification being removed from the circulation continuously and separated off in the water separator. The chloroform is then distilled off, the mixture is cooled to room temperature and the product which has crystallized out is filtered off with suction and washed with ethanol.

After drying, 232 g (0.9 mol) of N-carboethoxymethylene-4-chloroanthranilic acid are obtained.

This corresponds to a yield of 90%.

COMPARISON EXAMPLE 1 (preparation of the diethyl ester)

Reaction of N-carboxymethylene-4-chloroanthranilic acid in the presence of a large amount of acid as a catalyst (analogously to J. Heterocycl. Chem. 1987, 24, 812).

17.2 g (75 mmol) of N-carboxymethylene-4-chloroanthranilic acid are suspended in 170 ml (134.16 g) of ethanol and 40.3 g (390 mmol) of concentrated sulfuric acid are added in the course of 20 minutes. The mixture is heated at the boiling point for 24 hours.

According to HPLC analysis, the reaction mixture comprises 81% of the corresponding diethyl ester (ethyl N-carboethoxymethylene-4-chloro-anthranilate), and in addition 19% of an unidentified by-product.

N-Carboethoxymethylene-4-chloroanthranilic acid (i.e. the monoester) cannot be detected.

Isolation of the diester proves to be difficult, since after cooling the solution, filtering off the product which has precipitated out and washing it with ethanol, only 8 g of the diester are obtained, in the form of a viscous mass which cannot be crystallized. A further 2 g of product separate out as an oil by pouring the mother liquor onto water/ice.

COMPARISON EXAMPLE 2 (preparation of the dimethyl ester)

Reaction of N-carboxymethylene-4-chloroanthranilic acid in the presence of a large amount of acid as a catalyst (analogously to J. Heterocycl. Chem. 1987, 24, 812).

17.2 g (75 mmol) of N-carboxymethylene-4-chloro-anthranilic acid are suspended in 170 ml of methanol, and 40.3 g (390 mmol) of concentrated sulfuric acid are added in the course of 20 minutes. The mixture is heated at the boiling point for 24 hours and is then allowed to cool, and the product which has precipitated out is filtered off with suction.

After washing with methanol and drying, 12.2 g (47 mmol) of the corresponding dimethyl ester (methyl N-carbomethoxymethylene-4-chloro-anthranilate) are obtained, corresponding to a yield of 63%. N-Carbomethoxymethylene-4-chloro-anthranilic acid (i.e. the monoester) cannot be detected.

EXAMPLE 9

Preparation of N-carboethoxymethylene-6-fluoro-anthranilic acid

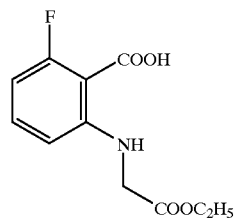

10.6 g of N-carboxymethylene-6-fluoro-anthranilic acid having a purity of 73% (corresponding to 39.6 mmol) are suspended in 25 ml of ethanol, 0.98 g (9.6 mmol) of concentrated sulfuric acid are added and the reaction mixture is heated under reflux for 6 hours. It is cooled to room temperature and the product which has precipitated out is filtered off with suction, washed with ethanol and dried.

5.6 g (23.2 mmol) of N-carboxymethylene-6-fluoro-anthranilic acid are obtained as a beige dyestuff, corresponding to a yield of 59%.

Melting point: 169° C.

To record the mass spectrum, the carboxyl group which is still free is esterified with diazomethane, since N-carboethoxymethylene-6-fluoroanthranilic acid decomposes on the GC column.

MS (methyl N-carboethoxymethylene-6-fluoro-anthranilate): 255, 226, 209, 182, 150.

EXAMPLE 10

Preparation of N-carboethoxymethylene-5-nitro-anthranilic acid with azeotropic distillation of water

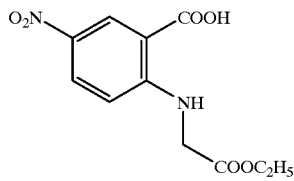

48 g of N-carboxymethylene-5-nitro-anthranilic acid having a purity of 61% (corresponding to 122 mmol) are suspended in 50 g of ethanol, and 1.96 g (19.2 mmol) of concentrated sulfuric acid are added. 145 g of chloroform are also added and the mixture is heated at the boiling point, the water formed during the esterification being removed from the circulation continuously and separated off in a water separator connected to the reaction vessel.

After 12 hours, a further 0.5 g (4.9 mmol) of concentrated sulfuric acid is added and the mixture is heated at the boiling point for another 6.5 hours, water being removed from the circulation.

250 ml of ethanol are then added, the chloroform is distilled off, the mixture is heated briefly at the boiling point, the precipitate is filtered off, the filtrate is concentrated and the product which has subsequently precipitated on cooling is filtered off. After drying, 31.0 g (116 mmol) in total (precipitate+product subsequently precipitated) of N-carboethoxymethylene-5-nitro-anthranilic acid are obtained as a pale yellow dyestuff, corresponding to a yield of 95%.

Melting point: 245° C.

To record the mass spectrum, the carboxyl group which is still free is esterified with diazomethane, since N-carboethoxymethylene-5-nitro-anthranilic acid decomposes on the GC column.

MS (methyl N-carboethoxymethylene-5-nitro-anthranilate): 282, 253, 209, 177, 131.

EXAMPLE 11

Preparation of N-carboethoxymethylene-3-chloro-anthranilic acid

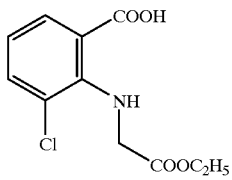

11.4 g of N-carboxymethylene-3-chloro-anthranilic acid (purity according to GC analysis: 52%, corresponding to 25.8 mmol) are suspended in 25 ml of ethanol, and 0.98 g (9.6 mmol) of concentrated sulfuric acid are added.

The mixture is heated at the boiling point for 3 hours and is then allowed to cool, and the product which has precipitated out is filtered off with suction, washed with cold ethanol and dried in vacuo.

5.0 g (19.4 mmol) of N-carboethoxymethylene-3-chloro-anthranilic acid are obtained as a yellow solid, corresponding to a yield of 75%.

Melting point: 175° C.

To record the mass spectrum, the carboxyl group which is still free is esterified with diazomethane, since N-carboethoxymethylene-3-chloro-anthranilic acid decomposes on the GC column.

MS (methyl N-carboethoxymethylene-3-chloro-anthranilate): 273, 271, 242, 227, 225, 212, 200, 198, 184, 182, 168, 166.

EXAMPLE 12

Preparation of N-carboethoxymethylene-4-chloro-anthranilic acid with azeotropic distillation of water 23 g (100 mmol) of N-carboxymethylene-4-chloro-anthranilic acid are suspended in 22 g of ethanol, and 1.1 g (10.7 mmol) of concentrated sulfuric acid are added. 50 g of 4-methyl-2-pentanone are also added and the mixture is heated at the boiling point for 3 hours, the water formed during the esterification being removed from the circulation continuously and separated off in a water separator connected to the reaction vessel.

The reaction mixture is then allowed to cool to room temperature, and the product which has precipitated out is filtered off, washed with ethanol and dried. 18.3 g (71 mmol) of N-carboethoxymethylene-4-chloro-anthranilic acid are obtained, corresponding to a yield of 71%.

We claim:

1. A compound of the formula (II)

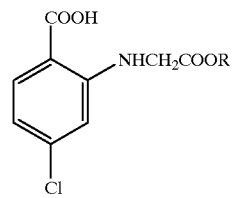

(II)

in which R is a straight-chain or branched $(C_1-C_{20})$-alkyl, phenyl or $CH_2$-phenyl, where the alkyl group or phenyl group can be substituted by halogen, $(C_1-C_4)$-alkyl or $(C_1-C_4)$-alkoxy.

2. A compound as claimed in claim 1, in which, in the compound of the formula (II), R is a straight-chain or branched $(C_1-C_{12})$-alkyl, phenyl or $CH_2$-phenyl.

3. A compound as claimed in claim 1, in which, in the compound of the formula (II), R is straight-chain or branched $(C_1-C_6)$-alkyl or phenyl.

4. N-Carboethoxymethylene-4-chloroanthranilic acid, N-carbo-methoxymethylene-4-chloroanthranilic acid, N-carboisopropoxymethylene-4-chloroanthranilic acid, N-carbopropoxymethylene-4-chloroanthranilic acid, N-carbobutoxymethylene-4-chloroanthranilic acid, N-carbohexoxymethylene-4-chloroanthranilic acid or N-carbobenzoxymethylene-4-chloroanthranilic acid.

* * * * *